(12) United States Patent
Jia et al.

(10) Patent No.: US 8,235,718 B2
(45) Date of Patent: Aug. 7, 2012

(54) DENTAL COMPOSITE

(75) Inventors: Weitao Jia, Wallingford, CT (US);
Shuhua Jin, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 838 days.

(21) Appl. No.: 11/676,807

(22) Filed: Feb. 20, 2007

(65) Prior Publication Data

US 2008/0199826 A1    Aug. 21, 2008

(51) Int. Cl.
*A61C 19/00* (2006.01)
(52) U.S. Cl. ......................................................... 433/26
(58) Field of Classification Search .................... 433/26, 433/203.1
See application file for complete search history.

(56) References Cited

U.S. PATENT DOCUMENTS

| | | | |
|---|---|---|---|
| 4,657,399 A | 4/1987 | Hall | |
| 4,802,850 A * | 2/1989 | Boon | 433/26 |
| 5,240,414 A * | 8/1993 | Thompson | 433/26 |
| 5,498,157 A | 3/1996 | Hall | |
| 5,906,490 A | 5/1999 | Kramer Primus et al. | |
| 6,499,998 B2 | 12/2002 | Kerschbaumer et al. | |

FOREIGN PATENT DOCUMENTS

EP    0591958    6/1998

OTHER PUBLICATIONS

Vident, 3-D Master Shade Guide, 1998-2008.*
Vident, Dental Technology Update, Winter 2006.*

* cited by examiner

*Primary Examiner* — Ralph Lewis
(74) *Attorney, Agent, or Firm* — Cantor Colburn LLP

(57) ABSTRACT

The shade system contains a set of dentin/body shades, and a set of enamel and opaque shades that correspond to the dentin/body shades. The system may also include tints and specialty incisals to provide special effects, if necessary.

17 Claims, No Drawings

DENTAL COMPOSITE

TECHNICAL FIELD

This invention relates to dental materials and techniques for making natural-looking dental restorations.

BRIEF DESCRIPTION OF THE RELATED ART

Many of the currently available dental composite systems rely on the knowledge and expertise of the dentist to create natural looking restorations. The systems and kits on the market today do not provide a defined, organized and simple technique. Many require complex layering techniques and expertise in mixing shades and colors to provide the correct color and translucency.

Color is communicated in terms of hue, chroma and value all of which affect the final shade perceived by the eye. Hue is the base color, i.e., Red, Yellow and Blue. Chroma is the saturation, or intensity, of the hue i.e. light blue is low in chroma while royal blue is high in chroma; both colors are blue in hue. Value is the greyness of the color ranging from black (lowest value) to pure white (highest value).

There is another aspect of color when discussing the natural appearance of tooth structure and that is opacity. Opacity is defined as the amount of light that is reflected back from an object that affects our perception of its depth. An object that is translucent has a level of transparency as light is transmitted through the object and we perceive depth with a potential ability to see through the object. Clear glass transmits 100% of light; it is transparent and we can see straight through it. An object that is 100% opaque, reflects 100% of light and we perceive it as solid with no depth.

With these concepts of color and opacity, we can better understand not only the structure of the natural tooth, but how the materials that compose it contribute to its natural appearance and beauty. It is the recreation of the natural anatomy of a tooth with regard to hue, chroma, value and opacity that makes a dramatic difference in the beauty and vitality of a direct composite restoration.

The art of placing layers, or increments, of various shades and opacities is not new to dentistry; it was perfected many years ago by dental laboratories through their production of highly esthetic ceramic restorations. However, the concept of replacing tooth structure with direct composite materials that optically match the structure being replaced is still foreign to many dentists today.

The concept of direct composite layering is simple. There are three optically distinct layers that make up the primary structure of the natural tooth: (1) Enamel: An optically translucent material with only a minor degree of intrinsic hue, natural enamel varies in thickness from the cervical third to the incisal edge becoming thickest in the incisal third. Enamel provides enough transparency at the incisal edge for edge effects to be readily seen against the dark oral cavity; (2) Intermediate or Shallow Dentin—This superficial dentin layer is responsible for imparting 98% of the perceived color of natural dentition. Unless intrinsic stains are present, intermediate dentin is consistently monochromatic; (3) Deep Dentin—Deep dentin is usually more opaceous and more chromatic than intermediate dentin. This anatomical layer rarely influences the appearance of the natural tooth unless genetic or developmental staining is present or staining has been imparted from heavy metal pigments.

There is a need to provide an easy and user-friendly process for making composite dental restorations. It is preferable that the process provide natural-looking restorations.

SUMMARY OF THE INVENTION

These and other objects and advantages are accomplished by the dental composite shade system provided herein and the method of using the system. The shade system contains a set of Dentin/Body shades, and a set of Enamel and Opaque shades that correspond to the Dentin/Body shades. The system may also include Tints and Specialty Incisals to provide special effects, if necessary.

The Composite Shade System is simple and easy to use, eliminating complex layering and shading techniques.

DETAILED DESCRIPTION OF THE PREFERRED EMBODIMENTS

This new dental composite shade system was created to provide a simplified approach to the complex problem of consistently generating polychromatic, layered restorations that mimic and enhance the natural beauty and diversity of human dentition quickly, easily and dependably. This system accomplishes this through careful shading of a full line of dentin/body shades and a limited line of translucent enamels and opaques.

This composite system can be adapted to nearly any existing technique of layering and delivery due to the accuracy of the shading. The shades are perfectly coordinated and easy to understand making the product required easy to select. The dental industry uses a variety of shades to create dental restorations that mimic natural teeth. There is not one standard system to measure and determine tooth color, but one very popular system in the dental industry is the Vita® Shade Guide. The Vita® Shade Guide offers four basic hue ranges: A, B, C, and D divided in the following sixteen shades: A1, A2, A3, A3.5, A4, B1, B2, B3, B4, C1, C2, C3, C4, D2, D3 and D4. The A shades are reddish brown in color; the B shades are reddish yellow; the C shades are grey; and the D shades are reddish grey. Studies have shown that the base shade of natural teeth will fall into the A range 70% of the time, with 20% in the D range, and only 10% in the B or C range. With the popularity of vital tooth bleaching consistently growing, the demand for Bleach shades grows as well. Another system in the industry, the Vita 3-D® Master Guide, provides bleach shades designated as OM1, OM2, and OM3, with OM1 being the highest in value, or the whitest.

Many other systems have been developed using these standard Vita® shades. For many dentists, this shade system is merely the starting point. Shading to match as closely as possible the remaining teeth in a patient's mouth is a very complicated process entailing application of multiple layers of colors, stains, etc. The selection of the correct color becomes a matter of luck and is strongly dependent on the expertise and skill of the dentist.

This new dental composite shading system herein provides a simplified approach to the complex problem of consistently generating polychromatic, layered restorations that mimic and enhance the natural beauty and diversity of human dentition quickly, easily and dependably. The system herein provides a series of dentin/body shades based on the sixteen basic shades in the Vita® system. Additionally, the system herein may include four bleach dentin/body shades that are white shades to match teeth that have been whitened.

The applicants herein have developed a line of enamels and opaque shades that coordinate easily with the sixteen dentin/ body shades and the bleach shades. The dentin/body shades include the following shades: A1, A2, A3, A3.5, A4, B1, B2, B3, B4, C1, C2, C3, C4, D2, D3, D4, Bleach, Extra Bleach, Super Bleach, and White Bleach. The enamels include the following shades: A Enamel, B Enamel, C Enamel, D Enamel, and Bleach Enamel. The system is easy to follow because the A Enamel may be used with any of the A dentin/body shades: A1, A2, A3, A3.5, A4; the B Enamel may be used with any of the B dentin/body shades: B1, B2, B3, B4; the C Enamel may be used with any of the C dentin/body shades: C1, C2, C3, C4; the D Enamel may be used with any of the D dentin/body shades: D2, D3, D4; and the Bleach Enamel may be used with any of the Bleach shades: Bleach, Extra Bleach, Super Bleach, and Ultra Bleach.

Likewise, the opaque shades are provided as: A Opaque, B Opaque, C Opaque, D Opaque, and Bleach Opaque. As with the enamels, A Opaque may be used with any of the A dentin/body shades: A1, A2, A3, A3.5, A4; the B Opaque may be used with any of the B dentin/body shades: B1, B2, B3, B4; the C Opaque may be used with any of the C dentin/body shades: C1, C2, C3, C4; the D Opaque may be used with any of the D dentin/body shades: D2, D3, D4; and the Bleach Opaque may be used with any of the Bleach shades: Bleach, Extra Bleach, Super Bleach, and Ultra Bleach.

Each dentin/body shade has been carefully formulated to blend easily with natural dentition as the primary dentin replacement material. Due to the advanced optical properties and unique "chameleon" effect inherent in their formulation, the dentin/body shades draw in the color of the surrounding cavosurface margin to generate nearly seamless restorations even when a polychromatic restoration is not required due to location or visibility in the smile line.

The optical properties of the translucent enamel material impart a true polychromatic effect with little to no effort on the part of the clinician. Each shade class (A, B, C, D, & Bleach) is represented, and the optics of each enamel is perfectly formulated to work with each corresponding range of dentin/body shades. Whether the dentin/body Shade is A-1, A-3 or any A shade, the recommended corresponding translucent enamel shade is A-Enamel. No technical or "artsy" shade names come attached to this system, just simple, intuitive nomenclature that makes good sense for quick shade selection and highly esthetic results.

When a case calls for masking of stained substrate dentin or a change in natural chroma according to patient demand, the opaques provide the right level of opacity to block out undesirable effects while contributing to the overall beauty of the final restoration. Like the enamels, the opaques have been perfectly formulated to coordinate with the basic shade ranges represented by the dentin/body shades.

This system has deliberately eliminated a proliferation of shades in the opaque range to simplify the use and choice of this material. Since opaque shades are always used under body shades, the dentist merely needs to choose the opaque that coordinates with the basic shade range of the selected dentin/body, apply in the thinnest layer necessary to mask the undesirable substrate, then layer the selected dentin/body and corresponding enamel shades to create the final appearance of the restoration.

In addition to the dentin/body shades, enamel shades and opaque shades, the system includes highly pigmented tints and specialty incisals. If severe staining is required, it is most effectively masked by the opaques included in the highly pigmented tints. The tints may include the following colors: grey, blue, yellow, pink, white opaque, yellow opaque, ivory opaque and brown. The specialty incisals may include the following shades: clear and white. "Edge Effects" are defined as the broad and highly diverse subtleties of translucency and pigmentation found in the incisal ⅓ of most anterior teeth. This system offers two types of materials for achieving different types of edge effects: tints for internal characterization and specialty incisals for the creation of an incisal "halo" effect.

Tints are highly pigmented flowable composites shaded to represent the most common optical hues found in natural teeth and include three opaques designed to mask out deep intrinsic stains. When used to intensify color at the incisal edge, the tints are applied sparingly prior to the enamel overlay to impart subtle to more striking internal color effects in the final restoration.

All of the materials and shades offered in this composite system are carefully formulated to provide the right hue, chroma and value required to effectively and reliably restore the look, beauty and vitality of natural dentition. The clinician must fully understand the effects of color in natural teeth in order to recreate the effect when practicing restorative dentistry. The nuances of color are communicated with very specific terminology that is detailed here for reference. This set of dental composite shades may also be used to make a set of dental shade guide device for assisting the dentist into making the correct choices in the fabrication of a dental restoration.

In natural teeth, each layer possesses unique color characteristics and optical properties that yield the polychromatic natural work of art that we see in human dentition. The System herein and its corresponding technique are designed to recreate the anatomy of natural dentition in the simplest way feasible. In reality, this technique is really an "anatomical" technique. Each of the three opacities provided in this system (opaque, dentin/body and enamel) is optically formulated to replicate the corresponding layer of natural dentition. When placed in anatomical layers mimicking natural teeth, a vital, esthetic, natural-looking restoration is readily and reliably created.

The following Table provides the percent opacity of each shade in the system. The measurements are based on 1.05±0.05 mm thickness with a diameter of 15 mm for all the composite material, except the Tints, which were measured based on 0.5 mm thickness discs.

TABLE 1

| Shades | Opacity (%) |
|---|---|
| Dentin/Body Shades | |
| A0 | 62 |
| A1 | 64 |
| A2 | 62 |
| A3 | 64 |
| A3.5 | 60 |
| A4 | 69 |
| B1 | 63 |
| B2 | 62 |
| B3 | 66 |
| B4 | 65 |
| C1 | 63 |
| C2 | 63 |
| C3 | 66 |
| C4 | 65 |
| D2 | 64 |
| D3 | 61 |
| D4 | 63 |
| Dentin Bleach Shades | |
| Bleach | 62 |
| Extra Bleach | 64 |

TABLE 1-continued

| Shades | Opacity (%) |
|---|---|
| Super Bleach | 62 |
| Ultra Bleach | 72 |
| Enamel Shades | |
| A Enamel | 44 |
| B Enamel | 41 |
| C Enamel | 47 |
| D Enamel | 45 |
| Bleach Enamel | 41 |
| Opaque Shades | |
| A Opaque | 72 |
| B Opaque | 73 |
| C Opaque | 75 |
| D Opaque | 78 |
| Bleach Opaque | 85 |

The tints include two tints of different white shades (White Opaque and Ivory Opaque) that have optical opacity of 95-100. Being in that opacity range, the materials can mask any dark colors underneath. The specialty incisals for the shades clear and white exhibit optical opacities of about 30 and 60, respectively, for 1.0 mm thickness.

The optical opacity is a relative scale expressed in percentage. The number 100 is the most opaque, while 0 is the least opaque, which is completely transparent in that case. The optical opacity described here is obtained by using Color-Walk Colorimeter, Model#2000 (Seradyn, Inc., IN)

As can be seen, the dentin/body shades have the optical opacities in the range of about 60-69, the opaques have opacities in the range of about 70-85, while the enamels have opacities of about 40-50. When layering those materials with different optical opacities as described, a natural tooth mimicking tooth filling can be achieved.

The composite compositions suitable for producing and achieving the various opacity leveled restorative materials are generally limitless. Examples include, but are not limited to, those materials as taught by Jia and Jia et al in U.S. Pat. Nos. 6,767,955, 6,730,715, 6,653,365, 6,417,246, 6,403,676, which are all hereby incorporated as references It is a histological fact that dentin imparts 98% of a tooth's hue or color. Though many dentists may have been taught in dental school to apply A3 in the gingival ⅓, then A2 in the middle ⅓ and A1 in the incisal ⅓, natural teeth are not made this way.

What imparts the appearance of varying degrees of color saturation from the cervical to the incisal aspects of a natural tooth is the thickness and tint of the translucent enamel overlay. Optically, enamel is basically colorless, largely serving to modulate the chroma of the underlying dentin.

Histologically, enamel is thinnest in the cervical ⅓, allowing the dentin color to appear more chromatic; this is why the cervical aspects of natural teeth appear more saturated or darker, not because the dentin itself is darker. As enamel approaches the middle ⅓ of the natural tooth, it gradually thickens as the underlying dentin begins to taper back toward the lingual aspect. As a result, the influence of the single dentin hue is reduced, and the value of the dentin visually lowers. In the incisal ⅓ of the tooth, dentin stops short of the incisal edge and the majority of the incisal ⅓ of the natural tooth is composed mostly of enamel. As enamel thickens, it displays a myriad of optical properties and color diversity, often exhibiting the undulations of dentin mammelons through the translucent incisal enamel. In the incisal zone, dramatic edge effects are often displayed in natural teeth.

If the clinician truly wishes to emulate nature and create beautiful restorations, anatomical layering is a requirement. There is no way to replicate the diversity of hue, chroma, value and opacity of anterior teeth with a single shade. By simply introducing an enamel layer onto the incisal two thirds of an anterior restoration, a true polychromatic restoration with all the optical properties of a natural tooth can be readily achieved. It is the outer enamel composite layer with its ideal transparency and slight hue that provides the modulation of chroma apparent in natural dentition. However, the degree of layering may vary according to the requirements of the case. This technique is designed to be flexible in this regard.

The use of the layering technique will provide the best results for all classes of restorations. Patient demand for esthetic anterior direct veneer, Class IV, and posterior inlay application restorations is high due to their direct impact on the smileline or general visibility, and the desired result is difficult to achieve with a single shade, regardless of material selected. The use of this technique reduces the reliance of the dentist on the dental lab for esthetic restorations in the anterior region. The benefits of this to the clinician and his or her practice are multifold ranging from the personal satisfaction of doing the job oneself, and doing it well, to reducing the treatment to a single visit thereby freeing up chairtime and maximizing profitability.

The method of using this composite shade system is now described.

The Vita® Classic and Vita® 3-D Bleach Guide may be used to take the base shade of the tooth to be restored. Shade tabs are held to the middle one-third of the tooth to be restored to determine the appropriate shade. Color correct lighting is used in this process and is highly recommended during this process. Also, the shade is taken before the tooth becomes desiccated through routine isolation. If the color of the existing dentition is to be changed or improved in the case of a smile makeover, the patient should be consulted to help determine the desired shade using the appropriate shade guide.

Next, the dentin/body shade of the composite shade system described herein is selected that corresponds directly to the most commonly used basic shade range, also referred to as the Vita® Shade Guide and the Vita® 3-D Bleach Guide. The dentin/body shade is applied to full contour in the cervical third of an anterior tooth and tapered lingually to provide room for the translucent enamel overly. The corresponding enamel shade is then selected. The enamel shade is easily chosen based on the dentin/body shade according to the basic shade range—A, B, C, D or Bleach. For example, if any A dentin/body shade is selected, the A Enamel will be selected; if any B Dentin/Shade is selected, the B Enamel will be selected and likewise for the C, D and Bleach dentin/body shades. In limited instances, the requirements of the case may require a departure from the recommended enamel shade. The clinician should use his or her judgment to achieve the desired end result.

The enamel shade is layered in the incisal two-thirds of the tooth to full contour resulting in the color of the dentin/body shade being most chromatic at the cervical third and slowly reducing in chroma and hue to the incisal edge imparting a translucent and polychromatic effect for the final restoration. For a posterior restoration, dentin/body is placed preferably with a vertical placement technique, avoiding the connection of opposing walls to avoid stress on the final restoration and post-operative pain. Dentin/body material is placed 0.5 to 0.75 mm shy of the cavosurface margin to provide room for the enamel layer. The enamel layer is placed to final contour using the anatomy of the natural tooth and adjacent dentition as a guide. If a polychromatic restoration is not required (i.e. a Class III restoration or a restoration not visible in the esthetic zone) an enamel may not be required as a single shade technique using dentin/body only may be used.

If masking of dentin staining or intrinsic color is required, a corresponding opaque shade is selected. As with the enamel shades, the opaque shade is chosen according to the dentin/body shade range—A, B, C, D or Bleach. This layer will be limited only to those areas where deep dentin is exposed or areas where minor "blocking out" of undesirable internal stains or hue is necessary. This material is also optimal for masking transition seams between a fractured tooth and the composite in a Class IV restoration. If dark, unsightly substrate is present such as Tetracycline stains, amalgam stains or metal posts or pins, it is recommended that the Universal or White Opaque Tint is applied in an ultra thin layer (less than 0.5 mm) after the selected adhesive system is applied and cured. The opaque tints are 100% opaque and can effectively mask most stains and undesirable substrates with minimal thickness. The opaque tints must be light cured prior to proceeding with layering of the restoration.

If edge effects are required or desired, the appropriate materials are selected to meet the requirements of the case. For internal characterization the selected shade is placed sparingly with a small artist brush or a #8 endo file on the dentin layer to be covered by enamel. The existing internal pigments present in adjacent teeth are thereby matched. It is important to note that all the opaque tints are for internal characterization or masking only. These tints are not to be used as external stains.

In order to create a halo effect, a thin ribbon of a selected specialty incisal is applied at the incisal edge of the restoration. The Clear Incisal shade will provide a more natural glow to the incisal edge, while the White Incisal shade will produce a more pronounced, whiter halo effect.

While the composite shade system herein provides a full range of materials and shades to meet the requirements of more complex esthetic cases and to suit the needs of master clinicians, the majority of esthetic cases may be effectively and beautifully created simply using the selected dentin/body shade and the corresponding enamel. When applied according to the recommended anatomical technique, it is possible to effectively recreate the optical properties of natural tooth structure with the application of only dentin/body and enamel materials of this composite shade system.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended embodiments.

What is claimed is:

1. A kit for making a layered dental composite restoration comprising:
    a plurality of basic dentin/body shades having four different hues, wherein each dentin/body shade is formulated for use as a primary dentin replacement material; and
    a set of four enamel shades that correspond to one of each of the four different hues in the dentin/body shades, wherein each enamel shade is formulated for use as a translucent material imparting a polychromatic effect to the layered dental composition restoration;
    wherein each one of the four enamel shades is formulated for use with a selected dentin/body shade from one of the four different hues in the plurality of dentin/body shades when, in making the layered dental composite restoration, a layer of a corresponding enamel shade is applied over a layer of the selected dentin/body shade to mimic natural teeth.

2. The kit of claim 1 further comprising a set of four opaque shades as materials that correspond to one of each of the four different hues in the dentin/body shades.

3. The kit of claim 2 further comprising a set of tints as materials to provide internal characterization to a layered dental restoration.

4. The kit of claim 3 further comprising a set of specialty incisals as materials to provide a halo effect to a layered dental restoration.

5. A shade guide device comprising tabs for use with the kit of claim 1 comprising:
    a plurality of basic dentin/body shades having four different hues comprising A1, A2, A3, A3.5, A4, B1, B2, B3, B4, C1, C2, C3, C4, D2, D3, D4; and
    a set of four enamel shades that correspond to one of each of the four different hues in the dentin/body shades comprising A Enamel, B Enamel, C Enamel and D Enamel.

6. The shade guide device of claim 5 further comprising a set of four opaque shades that correspond to one of each of the four different hues in the dentin/body shades comprising A Opaque, B Opaque, C Opaque, and D Opaque.

7. The shade guide device of claim 6 further comprising a set of tints to provide internal characterization to a dental restoration comprising grey, blue, yellow, pink, white opaque, yellow opaque, ivory opaque, and brown shades.

8. The shade guide device of claim 7 further comprising a set of specialty incisals to provide a halo effect to a dental restoration comprising a white and a clear shade.

9. The shade guide device of claim 5 wherein the dentin/body shades further comprise a set of bleach shades.

10. The shade guide device of claim 9 wherein the bleach shades comprise Bleach, Extra Bleach, Super Bleach, and Ultra Bleach.

11. The method of claim 1 wherein the percent opacity of the basic dentin/body shades is in the range of 70 to 85 percent and the percent opacity of the enamel shades is in the range of 40 to 50 percent and, wherein the measurements are based on 1.05 mm thickness with a diameter of 15 mm.

12. A kit for making a layered dental composite restoration comprising:

a plurality of basic dentin/body shades having four different hues comprising A1, A2, A3, A3.5, A4, B1, B2, B3, B4, C1, C2, C3, C4, D2, D3, D4, wherein each dentin/body shade is formulated for use as a primary dentin replacement material; and a set of four enamel shades that correspond to one of each of the four different hues in the dentin/body shades comprising A Enamel, B Enamel, C Enamel and D Enamel, wherein each enamel shade is formulated for use as a translucent material imparting a polychromatic effect to the layered dental composition restoration wherein each one of the four enamel shades is formulated for use with a selected dentin/body shade from one of the four different hues in the plurality of dentin/body shades when, in making the layered dental composite restoration, a layer of a corresponding enamel shade is applied over a layer of the selected dentin/body shade to mimic natural teeth.

13. The kit of claim 12 further comprising a set of four opaque shades as materials that correspond to one of each of the four different hues in the dentin/body shades comprising A Opaque, B Opaque, C Opaque, and D Opaque.

14. The kit of claim 13 further comprising a set of tints as materials to provide internal characterization to a dental restoration comprising grey, blue, yellow, pink, white opaque, yellow opaque, ivory opaque and brown shades.

15. The kit of claim 14 further comprising a set of specialty incisals as materials to provide a halo effect to a layered dental restoration comprising a white and a clear shade.

16. The kit of claim 12 wherein the dentin/body shades further comprise a set of bleach shades.

17. The kit of claim 16 wherein the bleach shades comprise Bleach, Extra Bleach, Super Bleach, and Ultra Bleach.

* * * * *